United States Patent
Flohr et al.

(10) Patent No.: US 11,278,255 B2
(45) Date of Patent: Mar. 22, 2022

(54) METHOD AND APPARATUS FOR PRODUCING A SPECTRAL COMPUTED TOMOGRAPHY IMAGE DATA SET

(71) Applicant: Siemens Healthcare GmbH, Erlangen (DE)

(72) Inventors: Thomas Flohr, Uehlfeld (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/022,289

(22) Filed: Sep. 16, 2020

(65) Prior Publication Data
US 2021/0085272 A1    Mar. 25, 2021

(30) Foreign Application Priority Data
Sep. 23, 2019   (EP) .................... 19198986

(51) Int. Cl.
*A61B 6/00*    (2006.01)
*A61B 6/03*    (2006.01)

(52) U.S. Cl.
CPC ............. *A61B 6/482* (2013.01); *A61B 6/032* (2013.01); *A61B 6/4021* (2013.01); *A61B 6/4241* (2013.01)

(58) Field of Classification Search
CPC ....... A61B 6/032; A61B 6/482; A61B 6/4241; A61B 6/4021; A61B 6/4014; A61B 6/405; A61B 6/5235; A61B 6/54; A61B 6/035; A61B 6/425; A61B 6/481; A61B 6/5258; G01T 1/2985; G01T 1/36; G06T 2211/408; G01N 23/046; G01J 11/00
See application file for complete search history.

(56) References Cited

U.S. PATENT DOCUMENTS

| | | | |
|---|---|---|---|
| 8,155,422 B2 | 4/2012 | Ziegler et al. | |
| 2005/0082491 A1 | 4/2005 | Seppi et al. | |
| 2010/0135557 A1 | 6/2010 | Krauss et al. | |
| 2018/0146938 A1* | 5/2018 | Allmendinger | A61B 6/5205 |

FOREIGN PATENT DOCUMENTS

DE    102007024158 A1    11/2008

OTHER PUBLICATIONS

Extended European Search Report for European Application No. 19198986.2 dated Feb. 18, 2020.

* cited by examiner

*Primary Examiner* — Courtney D Thomas
(74) *Attorney, Agent, or Firm* — Harness, Dickey & Pierce, P.L.C.

(57) ABSTRACT

A method is for producing a CT image data set via a detection unit with a photon-counting X-ray detector and configured to convert detected X-rays into measurement signals resolved at least into a first and a second energy range and, via an X-ray source unit, configured to emit X-rays having a first energy spectrum and having a different second energy spectrum. The method includes adapting the first and the second energy ranges, at least one limiting energy of each energy range being adapted; emitting X-rays of the first and second energy spectrum; detecting the emitted X-rays, at least one measurement signal being generated as a function of each respective energy range and the respective energy spectrum; producing the spectral CT image data set based upon the generated first and second measurement signals with the assistance of a spectral image processing technique; and outputting the spectral CT image data set.

20 Claims, 6 Drawing Sheets

METHOD AND APPARATUS FOR PRODUCING A SPECTRAL COMPUTED TOMOGRAPHY IMAGE DATA SET

PRIORITY STATEMENT

The present application hereby claims priority under 35 U.S.C. § 119 to European patent application number EP 19198986.2 filed Sep. 23, 2019, the entire contents of which are hereby incorporated herein by reference.

FIELD

Embodiments of the invention generally relate to a method, an apparatus, a computed tomography system and a computer program for producing a spectral computed tomography X-ray image data set.

BACKGROUND

Computed tomography (CT) is an imaging method which is primarily used for medical diagnostics. In CT, a radiation source, for example an X-ray source, and an X-ray detector cooperating therewith rotate about an object under examination, in particular a patient, to record spatially three-dimensional image data. During the rotational movement, "measured projection data" are in each case recorded within an angular sector. The measured projection data are a projection or plurality of projections containing information about the attenuation of the radiation by the object under examination from various projection angles. Based upon this measured projection data, also known as raw data sets, it is possible to reconstruct a two-dimensional cross-sectional image or a three-dimensional volume image of the object under examination, for example by way of "filtered back-projection" or by way of an iterative reconstruction method.

The measurement data also contains spectral information, since absorption in the object under examination is dependent on the energy of the X-rays, i.e. the energy of the X-ray photons, which pass through the object under examination. This spectral information may be indicative of the composition of the object under examination and make it possible to differentiate between different materials in the object under examination. However, it cannot conventionally be accessed via a conventional CT device with an energy-integrating X-ray detector.

One possible way of gaining access to the spectral information involves recording measured projection data with X-rays which have at least two mutually differing energy spectra, for example one energy spectrum with a low energy level and one with a higher energy level and jointly processing the resultant measurement data via a spectral data processing technique. It is known in this case to use "dual source" CT devices which have two angularly offset X-ray sources, each with an opposing X-ray detector, and wherein the two X-ray sources emit two energy spectra which differ from one another.

It is also known to use X-ray tubes with a "split filter", i.e. having a prefilter which is divided for example along the axis of rotation of the CT device, wherein two mutually differing energy spectra are emitted in different spatial regions and different regions of an X-ray detector are accordingly illuminated with different energy spectra. Another possibility which may be mentioned is "kV switching", wherein an X-ray source is used which is configured alternately to emit X-rays with two different energy spectra in rapid temporal succession by alternately switching in rapid temporal succession between two tube voltages.

In addition to using X-rays with at least two mutually differing energy spectra, spectral CT examinations can also be enabled by using energy-resolving X-ray detectors. A photon-counting, direct-converting X-ray detector may, for example, be used. Such X-ray detectors are capable of converting incident X-rays or photons into electrical pulses via a suitable converter material. CdTe, CZT, $HgI_2$, GaAs, or the like, may for example be used as the converter material. The electrical pulses are assessed by evaluation electronics, for example an integrated circuit (application specific integrated circuit (ASIC). In counting X-ray detectors, incident X-rays are then measured by counting the electrical pulses which are triggered by absorption of X-ray photons in the converter material. The height or also the length of a produced electrical pulse is generally proportional to the energy of the absorbed X-ray photon. In this manner, spectral information can be extracted by comparing the height or length of the electrical pulse with an energy threshold. If, for example, two energy thresholds are supplied for comparison, measurement signals may be generated or output which are resolved into two energy ranges which are defined by the two energy thresholds. Dual layer X-ray detectors which can enable access to spectral information are furthermore known.

SUMMARY

The inventors have discovered that in spectral CT examinations, one essential criterion for spectral raw data or image processing algorithm quality (e.g. for calculating base material images, for calculating pseudo-monoenergy images, or for classifying materials in the CT image) is the spectral separation of the at least two spectrally differing raw data sets or measurement data sets which are used for the spectral data processing technique. The inventors have discovered that it would be ideal to work with spectral input data sets which differ completely with regard to X-ray energy range, but this was not achievable with known methods.

At least one embodiment of the invention provides an improved method for producing a spectral CT image data set, wherein improved spectral separation of the measurement signals is enabled.

Further advantageous and in part per se inventive embodiments and developments of the invention are described in the claims and the following description.

The inventive solution of embodiments of the invention are described below with regard both to the method and to the apparatus. Features, advantages or alternative embodiments mentioned in this connection are likewise also transferable to the other claimed subjects and vice versa. In other words, the substantive claims (e.g. directed to an apparatus) may also be developed with the features which are described or claimed in connection with a method. The corresponding functional features of the method are here formed by corresponding substantive modules.

At least one embodiment of the invention relates to a method for producing a spectral computed tomography image data set (CT image data set) via a detection unit having at least one photon-counting X-ray detector and an X-ray source unit comprising adapting, emitting, detecting, producing and outputting.

The X-ray source unit of at least one embodiment is configured according to at least one embodiment of the invention to emit X-rays having a first energy spectrum and having a second energy spectrum which differs from the first. The X-ray source unit comprises at least one X-ray source for this purpose. The X-ray source may, for example, be configured as an X-ray tube. The X-ray source unit may, however, also comprise more than one X-ray source. In the case of a dual-source CT device, the X-ray source unit comprises for example two angularly offset X-ray sources which are arranged rotatably about a common axis of rotation around the object under examination in order to record measurement signals within different angular sectors.

At least one embodiment of the invention moreover relates to an apparatus for producing a spectral CT image data set. The apparatus according to at least one embodiment of the invention comprises:

an X-ray source unit configured to emit X-rays having a first energy spectrum and X-rays having a second energy spectrum which differs from the first, a detection unit having at least one photon-counting X-ray detector and configured to generate X-ray measurement signals based upon detected X-rays, which measurement signals are resolved at least into a first adaptable energy range and a second adaptable energy range, an adaptation unit configured to adapt the first energy range and the second energy range as a function of the first energy spectrum and the second energy spectrum, wherein in each case at least one limiting energy of a respective energy range is adapted, an image processing unit configured to produce the spectral CT image data set by way of a spectral image processing technique based upon the generated measurement signals, wherein at least one first generated measurement signal is included in the production as a function of the first energy range and the first energy spectrum and a second generated measurement signal as a function of the second energy range and the second energy spectrum, and an interface for outputting the spectral CT image data set.

At least on embodiment of the invention is directed to a method for producing a spectral computed tomography image data set via a detection unit including at least one photon-counting X-ray detector and configured to convert detected X-rays into measurement signals, resolved at least into a first adaptable energy range and a second adaptable energy range, and configured to emit, via an X-ray source unit, X-rays having a first energy spectrum and having a second energy spectrum which differs from the first energy spectrum, the method comprising:

adapting the first adaptable energy range and the second adaptable energy range as a function of the first energy spectrum and the second energy spectrum, respectively, via an adaptation unit, wherein at least one respective limiting energy, of each of a respective one of the first adaptable energy range and the second adaptable energy range, is adapted during the adapting;

emitting X-rays having the first energy spectrum and emitting X-rays having the second energy spectrum, via the X-ray source unit;

detecting the X-rays emitted having the first energy spectrum and detecting the X-rays emitted having the second energy spectrum, via the detection unit, wherein at least one first measurement signal is generated as a function of the first adaptable energy range and the first energy spectrum and wherein at least one second measurement signal is generated as a function of the second adaptable energy range and the second energy spectrum;

producing the spectral computed tomography image data set at least based upon the first measurement signals generated and the second measurement signals generated, with assistance of a spectral image processing technique, via an image processing unit; and outputting the spectral computed tomography image data set via an interface.

At least one embodiment is directed to an apparatus for producing a spectral computed tomography image data set comprising:

an X-ray source unit configured to emit X-rays having a first energy spectrum and configured to emit X-rays having a second energy spectrum, different from the first energy spectrum;

a detection unit including at least one photon-counting X-ray detector and configured to generate measurement signals based upon detected X-rays, the measurement signals being resolved at least into a first adaptable energy range and a second adaptable energy range;

an adaptation unit, configured to respectively adapt the first adaptable energy range and the second adaptable energy range as a function of the first energy spectrum and the second energy spectrum, wherein at least one limiting energy, of at least one of the first adaptable energy range and the second adaptable energy range, is generated;

an image processing unit configured to produce the spectral computed tomography image data set using a spectral image processing technique based upon the measurement signals generated, wherein at least one first generated measurement signal is included in production of the spectral computed tomography image data set as a function of the first adaptable energy range and the first energy spectrum and a second generated measurement signal is included in production of the spectral computed tomography image data set as a function of the second adaptable energy range and the second energy spectrum, an interface to output the spectral computed tomography image data set produced.

At least one embodiment is directed to an apparatus for producing a spectral computed tomography image data set comprising:

an X-ray source configured to emit X-rays having a first energy spectrum and configured to emit X-rays having a second energy spectrum, different from the first energy spectrum;

a detector including at least one photon-counting X-ray detector and configured to generate measurement signals based upon detected X-rays, the measurement signals being resolved at least into a first adaptable energy range and a second adaptable energy range;

at least one processor, configured to adapt the first adaptable energy range and the second adaptable energy range as a function of the first energy spectrum and the second energy spectrum, respectively, wherein at least one limiting energy, of at least one of the first adaptable energy range and the second adaptable energy range, is generated, and produce the spectral computed tomography image data set using a spectral image processing technique based upon the measurement signals generated, wherein at least one first generated measurement signal is included in production of the spectral computed tomography image data set as a function of the first adaptable energy range and the first energy spectrum and a second generated measurement signal is included in production of the spectral computed tomography image data set as a function of the second adaptable energy range and the second energy spectrum; and an interface to output the spectral computed tomography image data set produced.

At least one embodiment is directed to a computed tomography system comprising the apparatus of an embodiment.

BRIEF DESCRIPTION OF THE DRAWINGS

The invention is explained below with reference to example embodiments and to the appended figures. The depiction in the figures is schematic, highly simplified and not necessarily true to scale. In the figures.

DETAILED DESCRIPTION OF THE EXAMPLE EMBODIMENTS

Figure 1:
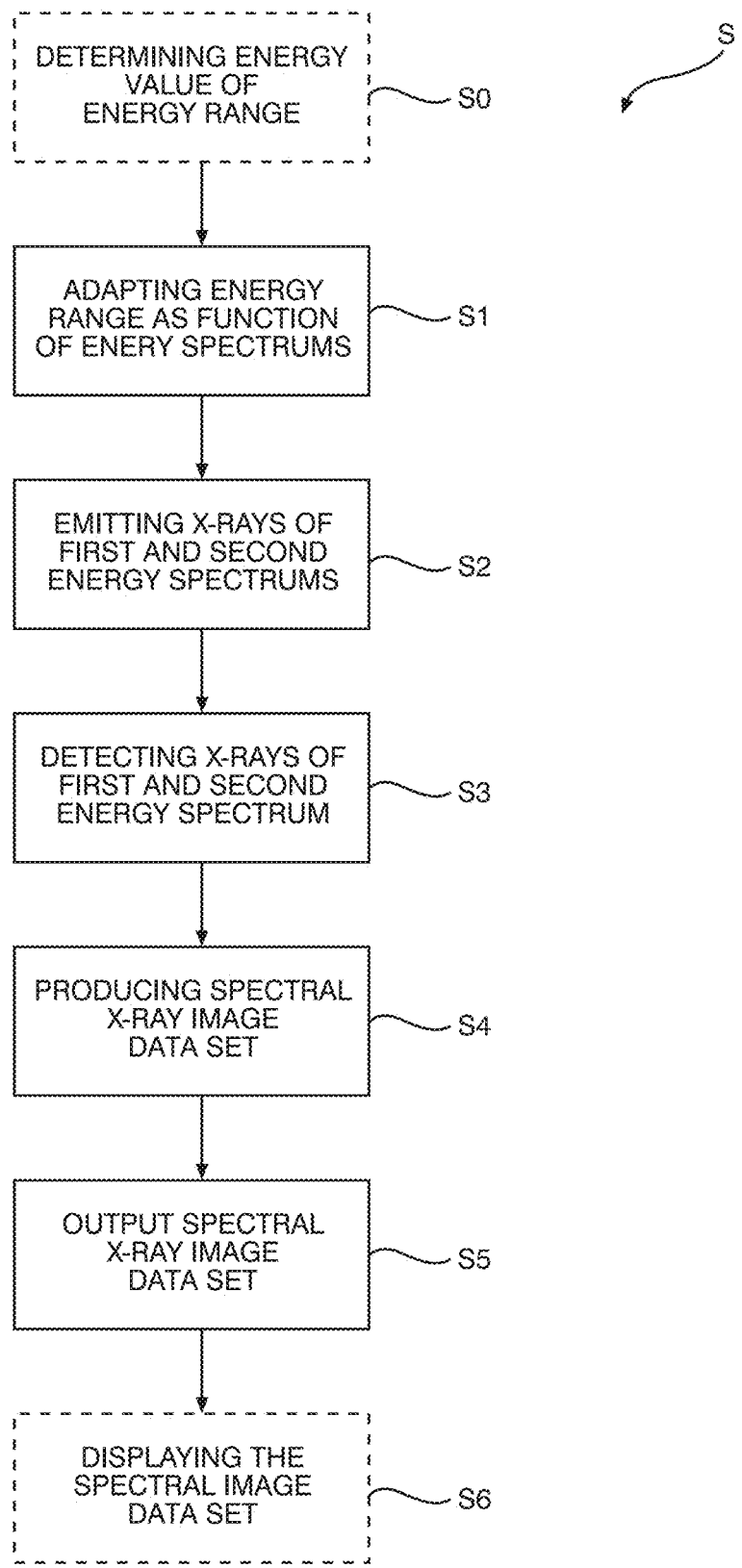
FIG. 1 is a schematic course of a method for producing a spectral computed tomography image data set.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for producing a spectral computed tomography image data set (CT image data set) via a detection unit having at least one photon-counting X-ray detector and an X-ray source unit comprising adapting, emitting, detecting, producing and outputting.

The X-ray source unit of at least one embodiment is configured according to at least one embodiment of the invention to emit X-rays having a first energy spectrum and having a second energy spectrum which differs from the first. The X-ray source unit comprises at least one X-ray source for this purpose. The X-ray source may, for example, be configured as an X-ray tube. The X-ray source unit may, however, also comprise more than one X-ray source. In the case of a dual-source CT device, the X-ray source unit comprises for example two angularly offset X-ray sources which are arranged rotatably about a common axis of rotation around the object under examination in order to record measurement signals within different angular sectors.

The X-ray source unit may be configured to emit the first and the second energy spectra by the at least one X-ray source being configured to emit not only the first but also the second energy spectrum simultaneously or with a time offset. The X-ray source unit may, for example, have an X-ray source which is configured to emit the first and the second energy spectra simultaneously in two different spatial regions, for instance via a split filter. The X-ray source may be configured for a kV switching method and temporally successively emit either the first or the second energy spectrum. The X-ray source unit may also be configured to emit the first and the second energy spectra by the X-ray source unit comprising two X-ray sources, wherein the first of the two X-ray sources for example emits the first energy spectrum, and the second of the two X-ray sources emits the second energy spectrum.

An energy spectrum of emitted X-rays substantially describes the distribution of the emitted X-ray photons as a function of photon energy. The first emitted energy spectrum may differ from the second energy spectrum in that the average emitted energy of the X-rays having the first energy spectrum differs from the average emitted energy of the X-rays having the second energy spectrum. The first and the second energy spectra may for example also differ in that the maximum emitted energy differs. The first energy spectrum may also differ from the second energy spectrum in that the minimum occurring energy which makes a substantial contribution to producing the CT image data set differs. The minimum occurring energy may for example be characterized by a sharp rise in the number of photons at the low-energy end of the energy spectrum. Two different energy spectra may preferably be produced for example by using two different tube voltages. Different energy spectra are also obtained by using different types of prefiltration which at least partially absorb the X-rays or by using different X-ray tube anode materials.

The detection unit according to at least one embodiment of the invention is configured to convert detected X-rays into energy-resolved measurement signals which are at least resolved into a first adaptable energy range and a second adaptable energy range. According to at least one embodiment of the invention, the detection unit has at least one photon-counting X-ray detector for this purpose.

The at least one X-ray detector here generally comprises a plurality of detection elements, also denoted pixels, in a linear or matrix arrangement. The at least one X-ray detector may here be composed of a plurality of detector modules, in each case having a subset of the plurality of detection elements of the X-ray detector. The at least one X-ray detector may here be understood to be a component which is assigned to and arranged opposite an X-ray source of the X-ray source unit and is illuminated by the latter to record measurement data, i.e. measurement signals. The object under examination is here positioned between the at least one X-ray detector of the detection unit and the assigned X-ray source of the X-ray source unit.

The detection unit may in particular be configured to convert detected X-rays into measurement signals which are resolved at least into a first adaptable energy range and a second adaptable energy range by the at least one photon-counting X-ray detector being configured to convert detected X-rays into energy-resolved measurement signals and provide them for further processing as a function of the first and the second adaptable energy ranges. It is likewise conceivable for the detection unit to have two photon-counting X-ray detectors, wherein the first energy range according to the invention may be supplied at least by a first photon-counting X-ray detector of the two X-ray detectors and the second energy range according to the invention at least by the second photon-counting X-ray detector of the two X-ray detectors. There may, however, also be other configurations. For example, both the first and the second photon-counting X-ray detectors may supply measurement signals as a function of both the first and the second energy ranges.

The photon-counting X-ray detector(s) may furthermore be configured to resolve detected X-rays into more than two energy ranges. Three, four or six energy ranges may, for example, be supplied. It may likewise be provided that the energy ranges for a number of detection elements of a photon-counting X-ray detector are adaptable, for example pixel-individually, such that not only the same but also locally different energy ranges may be supplied within the matrix of detection elements of a photon-counting X-ray detector for the production of measurement signals.

The photon-counting X-ray detector(s) may in particular be configured to supply energy-resolved measurement signals as a function of adaptable energy ranges for further processing by supplying adaptable energy thresholds for a comparison of the height or length of the electrical pulses produced in the X-ray detector by the incident X-rays. In particular, a lower and/or upper limiting energy of a respective energy range may be adaptable by way of an adjustable energy threshold.

In order to facilitate understanding, it is assumed in the following description that the first energy spectrum has at least a lower-energy average energy than the second energy spectrum. It is moreover hereinafter assumed that the first energy range covers a lower-energy region of X-ray photon energy in comparison with the second energy range according to the invention and the second energy range according to the invention covers a higher-energy energy range. This is not, however, intended to rule out the converse configuration. In converse embodiments, in which the first energy spectrum has a higher average energy than the second energy spectrum, the photon energy ranges covered by the first and the second energy ranges should be assigned conversely in the following description and the text of the description should be correspondingly mentally adapted.

In the adaptation step according to at least one embodiment of the invention, the first energy range and the second energy range are adapted as a function of the first energy spectrum and the second energy spectrum via an adaptation unit, wherein in each case at least one limiting energy of a respective energy range is adapted. Adaptation as a function of the first energy spectrum and the second energy spectrum may involve selecting and applying the respective at least one limiting energy as a function of the first and the second energy spectra. This may mean that the use of other energy spectra in particular leads to another at least one limiting energy and thus to other energy ranges.

At least one first, upper limiting energy of the lower-energy, first energy range may here be adapted which in particular corresponds to the maximum photon energy encompassed by the first energy range. At least one second, lower limiting energy of the second, higher-energy energy range may be adapted which in particular corresponds to the minimum photon energy encompassed by the second energy range. It may furthermore also be provided to adapt further limiting energies, for example a lower limiting energy of the lower-energy, first energy range or an upper limiting energy of the second, higher-energy energy range or limiting energies of further energy ranges which are supplied.

In variant embodiments, the first, upper limiting energy of the first energy range may be adapted to the same energy value as the second, lower limiting energy of the second energy range. Inasmuch as the first and the second energy ranges are supplied by a photon-counting X-ray detector, the first, upper limiting energy of the first energy range and the second, lower limiting energy of the second energy range may be adapted by way of an adaptable energy threshold. Once adapted, however, the respective limiting energies may also adopt different energy values. In particular, the first, upper limiting energy of the first energy range may be adapted to the same or a lower energy value than the second, lower limiting energy of the second energy range.

Adaptation as a function of the first and the second energy spectra may involve adapting the at least one limiting energy with regard to an optimized image quality, in particular with regard to image noise, image contrast or the occurrence of artifacts in the CT image data set produced by way of the first and the second energy spectra.

Adaptation may here in particular be based on an optimized energy value for the respective at least one limiting energy. The optimized energy value for the respective at least one limiting energy may correspond to that energy value which leads to an image quality which is desired or necessary for responding to a clinical question when the X-ray image data set is produced with energy ranges adapted on this basis.

The optimized energy value may be optimized with reference to a criterion, i.e. with reference to an optimization criterion, inter alia comprising for example an image noise value of the CT image data set or an image contrast value of the CT image data set. The optimized energy value may, for example, be optimized with regard to a contrast-to-noise ratio or a signal-to-noise ratio. In other words, applying the optimized energy value may for example enable an advantageously low noise level in the produced CT image data set. The optimized energy value may also be optimized with regard to a particularly advantageous material contrast between two materials. This may mean that applying the optimized energy value makes it particularly possible to differentiate or separate two materials, for example iodine and tissue with an X-ray absorption behavior similar to water, in the produced CT image data set.

The optimization criterion may also be an artifact value in the CT image data set which is associated with the occurrence of an artifact. The optimized energy value may, for example, be optimized with regard to the avoidance or reduction of one or more artifacts in the X-ray image data set. This may mean that, by applying the optimized energy value, an artifact occurs to a reduced extent in the produced X-ray image data set.

The optimization criterion may encompass the spectral overlap between the first energy spectrum and the second energy range and the second energy spectrum and the first energy range. In particular, the optimized energy value may be optimized with regard to a minimum spectral overlap simultaneously combined with the best possible dose utilization. This means for example that the first, upper limiting energy is set such that the first energy range overlaps as little as possible with the second energy spectrum, while simultaneously as few photons as possible of the first energy spectrum are not used for the production of the CT image data set. The equivalent applies to the second energy range. Minimizing the spectral overlap of the energy ranges and energy spectra may enable an improved spectral separation of the data sets based on the measurement signals. As a result, it is possible to produce particularly high quality X-ray image data sets by way of a spectral data processing technique.

An already determined, optimized energy value for the adaptation step may already be available, for example in the form of a database on a data storage medium, and be retrievable by the adaptation unit for the adaptation step via an interface. The optimized energy value may, however, also be determined close in time to the adaptation step.

The optimized energy value may for example be optimized by way of a machine learning method or also by way of an analytical method. A determination may, for example, be based on a plurality of measured or simulated (training) image data sets which are in each case based on measurement signals resolved into different energy ranges. By comparing different image data sets as a function of energy ranges or criteria derived therefrom, such as for instance an image noise value, an image contrast value or an artifact value, it is then possible to determine an optimized energy value for the respective at least one limiting energy. It is, however, also conceivable for the optimized energy value to be determined simply with reference to the first and the second energy spectra. Adaptation as a function of the first and the second energy spectra may then involve adapting the at least one limiting energy of the first energy range, in particular the first, upper limiting energy, as a function of the maximum emitted energy of the first energy spectrum and the minimum emitted energy of the second energy spectrum. It is likewise conceivable for adaptation to be carried out as a function of the average energy of the first and/or second energy spectrum, an integral over at least part of the first and/or second energy spectrum, or a sharply rising or sharply falling flank of the first and/or second energy spectrum. This may likewise apply to the at least one limiting energy of the second energy range, in particular the second, lower-energy limiting energy.

For example, one conceivable variant embodiment is for an operator to be able to input an item of information about the first and the second energy spectra via an input unit, on which basis the optimized energy value is retrieved or determined. The item of information may for example be the tube voltage of an X-ray tube or a prefilter which are used. It is likewise conceivable for a specific type of medical examination to be associated with a first and a second energy spectrum and, based upon an input of a type of medical examination, the optimized energy value is retrieved or determined. It is also conceivable for information about the first and the second energy spectra to be derived directly from the emitted first and second X-rays, on which basis the optimized energy value can be retrieved or determined.

Adaptation of the energy ranges can be carried out fully automatically via the adaptation unit, as soon as, for example, information is available about the type of examination or the energy spectra. Adaptation may involve confirmation by an operator, wherein a proposed adaptation, for example proposed energy ranges or limiting energies, is not implemented until it has been confirmed. For example, once the first and the second energy spectra have been specified, the respective at least one limiting energy may be fully or at least partially automatically adapted via the adaptation unit.

In the emission step according to at least one embodiment of the invention, X-rays having the first energy spectrum and having the second energy spectrum are emitted via the X-ray source unit. The first and the second energy spectra may be emitted simultaneously or with a time offset via one or more X-ray sources, for example X-ray tubes. An X-ray source is in each case configured to emit the X-rays towards an X-ray detector assigned thereto.

In the detection step, the emitted X-rays having the first energy spectrum and having the second energy spectrum are detected via the detection unit, in particular after having passed through an object under examination, wherein at least one first measurement signal is generated as a function of the first energy range and the first energy spectrum and at least one second measurement signal as a function of the second energy range and the second energy spectrum. The first measurement signal and the second measurement signal may be generated by the same photon-counting X-ray detector. In the case of two photon-counting X-ray detectors, the first measurement signal may also be generated by the first of the two photon-counting X-ray detectors and the second measurement signal by the second of the two photon-counting X-ray detectors. In addition to the first and the second measurement signals, further measurement signals may also be generated.

The emission and detection steps proceed substantially simultaneously during a rotational movement of the detection unit and X-ray source unit about the object under examination. In this manner, in each case first and second measurement signals can be recorded from different angular sectors, on which basis the spectral CT image data set can be produced.

Supplying the first measurement signal as a function of the first energy spectrum and the second measurement signal as a function of the second energy spectrum which differs from the first enables improved application of a spectral image processing technique for producing the X-ray image data set. In the production step according to the invention, the spectral CT image data set is accordingly produced at least based upon the generated first and generated second measurement signals by an image processing unit with the assistance of a spectral image processing technique. Production may in particular be based on a plurality of first measurement signals and a plurality of second measurement signals which were in each case recorded from different angular sectors. In the field of CT image processing, a person skilled in the art is here familiar with a plurality of spectral image processing techniques, for example for calculating base material images, for calculating pseudo-mono-energy images, or for classifying materials in the CT image data set, and therefore no further explanations will be provided here in this respect.

The produced spectral CT image data set is then output according to at least one embodiment of the invention via an interface. The X-ray image data set and, for example, a finding based thereon may be output for a user on a display unit for displaying the X-ray image data set. The X-ray image data set may also be output to a further processing unit which further processes the data set. Structures may, for example, be segmented or measured on this basis.

The recorded measurement data sets can only be inadequately separated on an energy basis by making use of any one of the above-stated methods (dual source, kV switching, split filter, energy-resolving detector) alone for recording spectral CT measurement data. While known methods which are based on recording two CT data sets with different tube voltages, such as for instance "dual source" systems or "kV switching" systems in combination with an integrating detector, do indeed give rise to a different average energy of the two input data sets, the two data sets overlap considerably in the energy range up to maximum energy of the data set recorded with the lower tube voltage. In methods with "dual layer" detectors, a spectral overlap of the two data sets over the entire energy range is obtained. Conventional use of a photon-counting detector with two or more energy ranges also fails to provide data which is clearly divided into said ranges in energy terms. The CT measurement data recorded in the individual energy ranges exhibits a spectral overlap due to physical effects such as charge sharing (of an event) between adjacent detector elements or fluorescence in the detector material which is characterized in that higher energy X-ray quanta are incorrectly registered with an excessively low energy, i.e. in low-energy energy ranges. The spectral overlap may impair the quality of spectral algorithms, amplify image noise and increase the level of artifacts present in the result images produced with these algorithms. Spectral overlap ultimately results in distinct limitations and higher radiation dose requirements for spectral CT examinations.

The inventors have recognized that, thanks to the combination of a detection unit having at least one photon-counting X-ray detector and configured to convert detected X-rays into measurement signals which are resolved at least into a first adaptable energy range and a second adaptable energy range, with an X-ray source unit which is configured to emit X-rays having a first energy spectrum and having a second energy spectrum which differs from the first, it is possible to ensure improved spectral separation by a first measurement signal advantageously being supplied for production as a function of the first energy range and the first energy spectrum and a second measurement signal as a function of the second energy spectrum and the second measurement signal. The first and second energy ranges are here advantageously adapted to the first and the second energy spectra. The inventive method consequently advantageously enables the production of higher quality spectral CT image data sets by it being possible to supply optimized measurement signals, i.e. data sets optimized for the spectral data processing technique.

It may be provided in one advantageous configuration of at least one embodiment of the invention that, in the adaptation step, the respective at least one limiting energy of the first energy range and the second energy range is automatically adapted via the adaptation unit as a function of the spectral image processing technique, a type of medical examination and/or an item of patient-specific information.

This aspect of at least one embodiment of the invention is based on the consideration that the image quality of the image data set may be optimized in that different image processing techniques may optionally place different demands on the supplied measurement signals. Adaptation of the energy ranges or the respective at least one limiting energy of the first and the second energy ranges as a function of the spectral image processing technique may then advantageously lead to improved image quality.

The inventors have likewise recognized that the image quality of the produced image data set may be optimized in that energy ranges are adapted in the light of the type of examination, since different types of examination may optionally place different demands on the X-ray image recording or on the supplied measurement signals. One type of examination may moreover be associated with used energy spectra or with a used spectral data processing technique, on which basis an optimized adaptation may advantageously proceed via the adaptation unit.

A type of examination should here be taken to mean any desired medical or clinical question which can be answered with reference to X-ray image recordings. For example, an examination of blood vessels may proceed by way of an angiography recording or an examination of the liver parenchyma, in each case with administration of contrast agent, or an examination of bone tissue without contrast agent. Adaptation may then proceed as a function of the type of examination, in particular of the planned type of examination which is to proceed with reference to the produced CT image data set for the patient.

The inventors have likewise recognized that the image quality of the produced CT image data set may also be optimized in that energy ranges are adapted in the light of an item of patient-specific information. This aspect of at least one embodiment of the invention is based on the consideration that the patient, i.e. the object under examination, may, by attenuation of the X-rays in the patient, have an impact on the energy spectrum behind the patient and thus differently adapted energy ranges are optionally advantageous for production for different patients or different regions of the patient. The emitted energy spectra are furthermore often selected based upon patient-specific information, such that it is possible by this means to derive information about the energy spectra used which can advantageously be put to use for automatic adaptation of the energy ranges.

An item of patient-specific information may be an item of patient-specific body-related information about the patient of whom a computed tomography image data set is to be produced. The item of patient-specific information may for example comprise one of the following items of information: patient size, patient width, patient shape, patient weight and/or the patient's X-ray attenuation behavior. At least one or more items of patient-specific information may for example originate from an evaluation of a patient topogram, a photographic image of the patient or one or more X-ray image recordings of the patient, for example from prior X-ray examinations. Alternatively, an item of patient-specific information about the patient may be determined by integrating scales for establishing patient weight into the patient couch of the X-ray image recording apparatus. In a further embodiment, patient-specific body-related information may also be input by a user via an input unit.

For example, specific energy values for the respective at least one limiting energy or a first and a second energy spectrum, or retrievable functions in the form of arithmetic functions or in the form of machine learning systems may be available for determining energy values associated with a selection of spectral image processing techniques, types of medical examinations and/or patient-specific information or information derived therefrom. In the context of a spectral CT examination, a specific spectral image processing technique, a type of medical examination and/or an item of patient-specific information may be specified or determined. On this basis, an energy value for the respective at least one limiting energy may be retrieved or determined by way of a retrievable function and the energy ranges automatically adapted via the adaptation unit.

One configuration for the purposes of at least one embodiment of the invention may accordingly provide that, prior to production of the CT image data set, an operator, i.e. user, specifies or inputs via an input unit configured for this purpose a spectral data processing technique, a type of examination or item of patient-specific information.

In one advantageous configuration, the method according to at least one embodiment of the invention moreover comprises determining an optimized energy value for the respective at least one limiting energy of the first energy range and of the second energy range at least based upon the first and the second energy spectra via an optimization unit.

The optimized energy value is preferably optimized with reference to a criterion from the following list:
an image noise value of the CT image data set,
an image contrast value of the CT image data set,
an artifact value of the CT image data set,
a spectral overlap value.

The spectral image processing technique, a type of medical examination and/or an item of patient-specific information may also be included here in this determination.

The determination step may here comprise application of a machine learning method. The determination step may also be based on an arithmetic method.

Determination may also be carried out via an artificial intelligence system, i.e. by a machine learning method. An artificial intelligence system may be taken to be a system for artificially generating knowledge from experience. An artificial system learns from examples in a training phase and, once the training phase is complete, is capable of generalizing. Using such a system may involve the recognition of patterns and regularities in the training data. The artificial intelligence system may be based on an artificial neural network, in particular a folding neural network or also on another machine learning method. In particular, after the training phase, an artificial intelligence system is capable of automatically identifying an optimized limiting energy in a particularly reliable and time-efficient manner.

A determination may, for example, be based on a plurality of measured or simulated (training) image data sets which are in each case based on measurement signals resolved into different energy ranges. By comparing different image data sets or criteria derived therefrom, such as for instance an image noise value, an image contrast value or an artifact value, it is then possible to determine an optimized energy value for the respective at least one limiting energy.

An optimized energy value may advantageously be supplied for adaptation.

The value may here also already be determined temporally independently in advance for a plurality of first and second energy spectra. The result which may then for example be supplied is a database which, as a function of the first and second energy spectra, the spectral image processing technique, the type of medical examination and/or patient-specific information, supplies respectively optimized energy values in a manner retrievable for the adaptation unit in the form of a database, for example a table or the like. Further parameters are moreover also conceivable.

In one embodiment variant, the determination step may have trained or adapted functions supplied retrievably which, as a function of the first and second energy spectra, the spectral image processing technique, a type of medical examination and/or an item of patient-specific information or also other parameters as input parameters, determine the optimized energy value and output it to the adaptation unit.

One advantageous further development of at least one embodiment of the invention here provides that the first energy range adjoins the second energy range.

In this configuration, the at least one limiting energy of the first and the second energy ranges in each case assumes a common energy value. This constitutes a particularly simple configuration with regard to the first and second energy ranges. Such a configuration may advantageously already be supplied by an individual photon-counting X-ray detector which provides just two energy thresholds for adapting the energy ranges. As a consequence, the determination of an optimized energy value can advantageously likewise be simplified by reducing the parameters.

In another embodiment of the invention, the first energy range and second energy range can be spaced apart from one another.

Spaced apart means that the first upper limiting energy of the first energy range adopts another, in particular lower, energy value than the second lower limiting energy of the second energy range, such that between the first energy range and the second energy range there is a further energy range which separates the first and the second energy ranges from one another.

It is advantageously possible as a consequence to ensure improved spectral separation of the generated measurement signals by for example at least part of an energy range in which the first energy spectrum optionally overlaps with the second energy spectrum being disregarded for image production or at least being less heavily weighted in production, whereas energy ranges with little or no spectral overlap make the substantial contribution to producing the spectral CT X-ray image data set.

In one simple variant of the method according to at least one embodiment of the invention, just the first measurement signals as a function of the first energy spectrum and of the first energy range and second measurement signals as a function of the second energy spectrum and of the second energy range enter into the production of the spectral X-ray image data set in order to achieve improved spectral separation of the data set based on the first energy spectrum and the data set based on the second energy spectrum.

One further advantageous development, however, further provides, in particular in the event that the first energy range adjoins the second energy range, moreover generating a third measurement signal as a function of the first energy spectrum and of the second energy range and a fourth measurement signal as a function of the second energy spectrum and of the first energy range, wherein the third and fourth measurement signals are moreover included in the production step.

Likewise, in particular in the event that the first energy range and the second energy range are spaced apart from one another, a third measurement signal is moreover generated as a function of the first energy spectrum and a third energy range and a fourth measurement signal as a function of the second energy spectrum and a fourth energy range, wherein the third and fourth measurement signals are moreover also included in the production step. The third energy range may for example encompass a higher-energy energy range which adjoins the first energy range and differs from the second energy range. The fourth energy range may for example encompass a lower-energy energy range which adjoins the second energy range and, however, differs from the first energy range. Further configurations of energy ranges are furthermore also possible.

Input of the third and fourth measurement signals advantageously means that as far as possible the entire available dose information may be utilized for producing the CT X-ray image data set, so optionally avoiding any unnecessary exposure of the patient to radiation.

The generated measurement signals may preferably be included in a manner weighted by way of weighting factors in the production of the CT image data set, wherein the first measurement signal is in particular more heavily weighted than the third measurement signal and the second measurement signal is in particular more heavily weighted than the fourth measurement signal.

Improved quantum utilization simultaneously combined with best possible spectral separation of the measurement data sets may advantageously be achieved.

In particular, use may be made of optimized weighting factors which are optimized based upon an image noise value of the X-ray image data set, an image contrast value of the X-ray image data set or an artifact value of the X-ray image data set. The optimized weighting factors for the respective measurement signals may correspond to those weighting factors which lead to an image quality which is desired or necessary for answering a clinical question when the X-ray image data set is produced on the basis thereof. The optimized weighting factors may for example be optimized by way of a machine learning method or also by way of another method.

Further energy ranges may moreover also be provided and further measurement signals accordingly generated in further advantageous developments. The most varied configurations resolved into two, three, four, five or more energy ranges are conceivable, the measurement signals of which may preferably also be included in production in a manner weighted by way of weighting factors. Resolution into more than two energy ranges may enable finer tuning of the energy ranges to the first and the second energy spectra and finer tuning of the measurement signal weights in the production step. Spectral separation may consequently optionally be improved while simultaneously ensuring the best possible quantum utilization of the administered X-rays.

In one further advantageous embodiment variant of the method according to at least one embodiment of the invention, either the first energy spectrum or the second energy spectrum is selectively alternately emitted in the emission step.

The method may advantageously be carried out via just one X-ray detector and one X-ray source. This variant of the method according to the invention may in particular be carried out by the X-ray source unit providing an X-ray source which is configured for a "kV switching" method. The disadvantage of such a configuration is the relatively high cost of supplying an X-ray source configured for this purpose.

One advantageous variant may furthermore provide that the detection unit has a photon-counting X-ray detector with a plurality of detection elements, wherein a first subset of the plurality of detection elements is illuminated with the first energy spectrum via the X-ray source unit and a second subset of the plurality is illuminated with the second energy spectrum and wherein the first measurement signal is generated via the first subset of the plurality of detection elements and the second measurement signal via the second subset of the plurality of detection elements.

The method may advantageously be carried out via just one X-ray detector and one X-ray source. In particular, this variant of the method according to at least one embodiment of the invention may be carried out with an X-ray source having a split filter. This may correspond to an inexpensive variant of the X-ray source. One drawback, however, is the lower adjustability of the emitted energy spectra and the resultant large overlap of the energy spectra up to the maximum emitted energy. However, in this case too, it is advantageously possible by way of the method to achieve improved image quality by supplying the first and second measurement signals and adapting the energy ranges as a function of the first energy spectrum and the second energy spectrum.

In addition, in one particularly advantageous embodiment of the method according to the invention, the detection unit may have a first photon-counting X-ray detector and, arranged at an angular offset thereto, a second photon-counting X-ray detector, and the X-ray source unit in each case has opposite thereto a first X-ray source which emits the first energy spectrum and a second X-ray source which emits the second energy spectrum, wherein the first measurement signal is generated via the first X-ray detector and the second measurement signal via the second X-ray detector.

Elevated flexibility and good spectral separation of the generated measurement data are advantageously achievable. Furthermore, even given the same number of energy thresholds, providing two photon-counting X-ray detectors enables elevated variability and adaptability of the energy ranges, since the X-ray detectors and the energy ranges thereof may in each case be adapted separately from one another.

At least one embodiment of the invention moreover relates to an apparatus for producing a spectral CT image data set. The apparatus according to at least one embodiment of the invention comprises:

an X-ray source unit configured to emit X-rays having a first energy spectrum and X-rays having a second energy spectrum which differs from the first, a detection unit having at least one photon-counting X-ray detector and configured to generate X-ray measurement signals based upon detected X-rays, which measurement signals are resolved at least into a first adaptable energy range and a second adaptable energy range, an adaptation unit configured to adapt the first energy range and the second energy range as a function of the first energy spectrum and the second energy spectrum, wherein in each case at least one limiting energy of a respective energy range is adapted, an image processing unit configured to produce the spectral CT image data set by way of a spectral image processing technique based upon the generated measurement signals, wherein at least one first generated measurement signal is included in the production as a function of the first energy range and the first energy spectrum and a second generated measurement signal as a function of the second energy range and the second energy spectrum, and an interface for outputting the spectral CT image data set.

The apparatus according to at least one embodiment of the invention for producing a spectral X-ray image data set may in particular be configured to carry out at least one embodiment of the previously described inventive method and the aspects thereof. The apparatus for producing a spectral X-ray image data set may be configured to carry out the method and the aspects thereof by the X-ray source unit, the detection unit, the adaptation unit, the image processing unit and the interface being configured to carry out the corresponding method steps.

The interface may in particular be configured to output the spectral CT image data set to an output unit, for example a display for displaying the image data set. The interface may likewise be configured to output the spectral CT image data set to a further processing unit.

In particular, the apparatus may moreover comprise an input unit for user input, for example in order to input information about the first energy range and the second energy range, the spectral image processing technique, a medical X-ray application and/or an object under examination.

In an advantageous configuration of the apparatus according to at least one embodiment of the invention, the X-ray source unit comprises an X-ray source with a split filter, which source is configured simultaneously to emit both the first energy spectrum and the second energy spectrum.

Alternatively, the X-ray source unit may have an X-ray source which is configured to switch over selectively and alternately between the first energy spectrum and the second energy spectrum.

Alternatively, it may also be provided that the detection unit has a first photon-counting X-ray detector and, arranged at an angular offset thereto, a second photon-counting X-ray detector, and the X-ray source unit in each case has opposite thereto a first X-ray source configured to emit the first energy spectrum and a second X-ray source configured to emit the second energy spectrum.

FIG. 1 shows a schematic course of a method according to an embodiment of the invention for producing a spectral CT X-ray image data set via a detection unit 7, having at least one photon-counting X-ray detector 71, 72, 73, 74 and configured to convert detected X-rays 4 into measurement signals which are resolved at least into a first adaptable energy range EB1 and a second adaptable energy range EB2, and configured to emit, via an X-ray source unit 3, X-rays 4 having a first energy spectrum 9 and having a second energy spectrum 10 which differs from the first.

The method has the adaptation step S1. The first energy range EB1 and the second energy range EB2 are here adapted via an adaptation unit 11 as a function of the first energy spectrum 9 and the second energy spectrum 10, wherein in each case at least one limiting energy GE1, GE2 of a respective energy range EB1, EB2 is adapted. The respective at least one limiting energy GE1, GE2 of a respective energy range EB1, EB2 may here be adapted with reference to an optimized energy value. In particular, the optimized energy value of the respective at least one limiting energy GE1, GE2 of a respective energy range EB1, EB2 may be determined in a determination step S0 via an optimization unit 25.

The determination S0 of the optimized energy value for the respective at least one limiting energy GE1, GE2 may be based at least on the first and the second energy spectra. In the determination step S0, the optimized energy value for the respective at least one limiting energy GE1, GE2 may moreover be optimized at least based upon a criterion from the following list:

an image noise value of the CT image data set,
an image contrast value of the CT image data set,
a material contrast value of the CT image data set,
an artifact value of the CT image data set, and
a spectral overlap value between the first energy spectrum and the second energy range and/or the second energy spectrum and the first energy range.

The determination step S0 may in particular be based on applying a machine learning method, for example via a trained neural network. It may, however, also be implemented in another manner.

It may moreover be provided in the adaptation step S1 that the respective at least one limiting energy GE1, GE2 of the first energy range EB1 and the second energy range EB2 is moreover automatically adapted via the adaptation unit 11 as a function of a spectral image processing technique, a type of medical examination and/or an item of patient-specific information.

It may be provided that the spectral image processing technique, the medical type of examination and/or the patient-specific information is also included in the determination step.

The method S furthermore comprises the emission step. X-rays 4 having the first energy spectrum 9 and having the second energy spectrum 10 are here emitted via the X-ray source unit 3.

The first energy spectrum 9 and the second energy spectrum 10 may be emitted simultaneously via an X-ray source 32 comprised by the X-ray source unit 3. This may for example be achieved via a split filter which is arranged as a prefilter on the X-ray source 32, wherein the first energy spectrum 9 and the second energy spectrum 10 may be emitted in two different spatial regions which are delimited from one another, such that one part of the X-ray-illuminated X-ray detector 72 is illuminated via the first energy spectrum 9 and a second part of the X-ray-illuminated X-ray detector 72 is illuminated via the second energy spectrum 10. The first energy spectrum 9 and the second energy spectrum 10 may also be emitted with a time offset via an X-ray source 31 comprised by the X-ray source unit 3, for example by applying the kV switching method, wherein the X-ray source 31 is configured to emit either the first energy spectrum 9 or the second energy spectrum 10 in rapid temporal succession.

The first energy spectrum 9 and second energy spectrum 10 may also be emitted by two different X-ray sources 33, 34 which are comprised by the X-ray source unit 3, by a first X-ray source 33 of the X-ray source unit 3 emitting the first energy spectrum 9 and a second X-ray source 34 of the X-ray source unit 3 emitting the second energy spectrum 10.

In the case of a dual-source CT device, the X-ray source unit 3 comprises for example two angularly offset X-ray sources 33, 34 which are arranged rotatably about a common axis of rotation 29 around the object under examination 21 in order to record measurement signals within different angular sectors.

In the detection step S3, the emitted X-rays 4 having the first energy spectrum 9 and having the second energy spectrum 10 are detected via the detection unit 7, wherein at least one first measurement signal is generated as a function of the first energy range EB1 and the first energy spectrum 9 and at least one second measurement signal as a function of the second energy range EB2 and the second energy spectrum 10.

Then, in a production step S4, the spectral X-ray image data set is produced at least based upon the generated first and the generated second measurement signals with the assistance of a spectral image processing technique via an image processing unit 13 and, in the output step S5, output via an interface 15. Such spectral image processing techniques are widely known in the field of CT image processing and will therefore not be explained any further here.

The spectral X-ray image data set may be output for example on a display unit 17 for displaying the spectral CT X-ray image data set or to a further processing unit for further processing of the spectral CT image data set.

It may be provided that just the first and the second measurement signals are included in production. Further measurement signals may furthermore be produced. For example, a third measurement signal may be generated as a function of the first energy spectrum 9 and the second energy range EB2 or as a function of the first energy spectrum 9 and a third energy range and a fourth measurement signal as a function of the second energy spectrum 10 and the first energy range EB1 or as a function of the second energy spectrum 10 of a fourth energy range, wherein the third and fourth measurement signals are moreover also included in the production step S5.

It may here be provided that, on production of the spectral CT image data set, the generated measurement signals are included in the image data set in a manner weighted via weighting factors, wherein the first measurement signal is in particular more heavily weighted than the third measurement signal and the second measurement signal in particular more heavily weighted than the fourth measurement signal.

In particular, optimized weighting factors may be used for this purpose which are optimized based upon an image noise value of the CT image data set, an image contrast value of the X-ray image data set or an artifact value of the CT image data set. The optimized weighting factors for the respective measurement signals may correspond to those weighting factors which lead to an image quality which is desired or necessary for answering a clinical question when the CT image data set is produced on the basis thereof.

The method may comprise a further step S6 of displaying the spectral CT image data set, wherein the spectral CT image data set is displayed for an operator on a display unit 17, for example a display.

Figure 2:
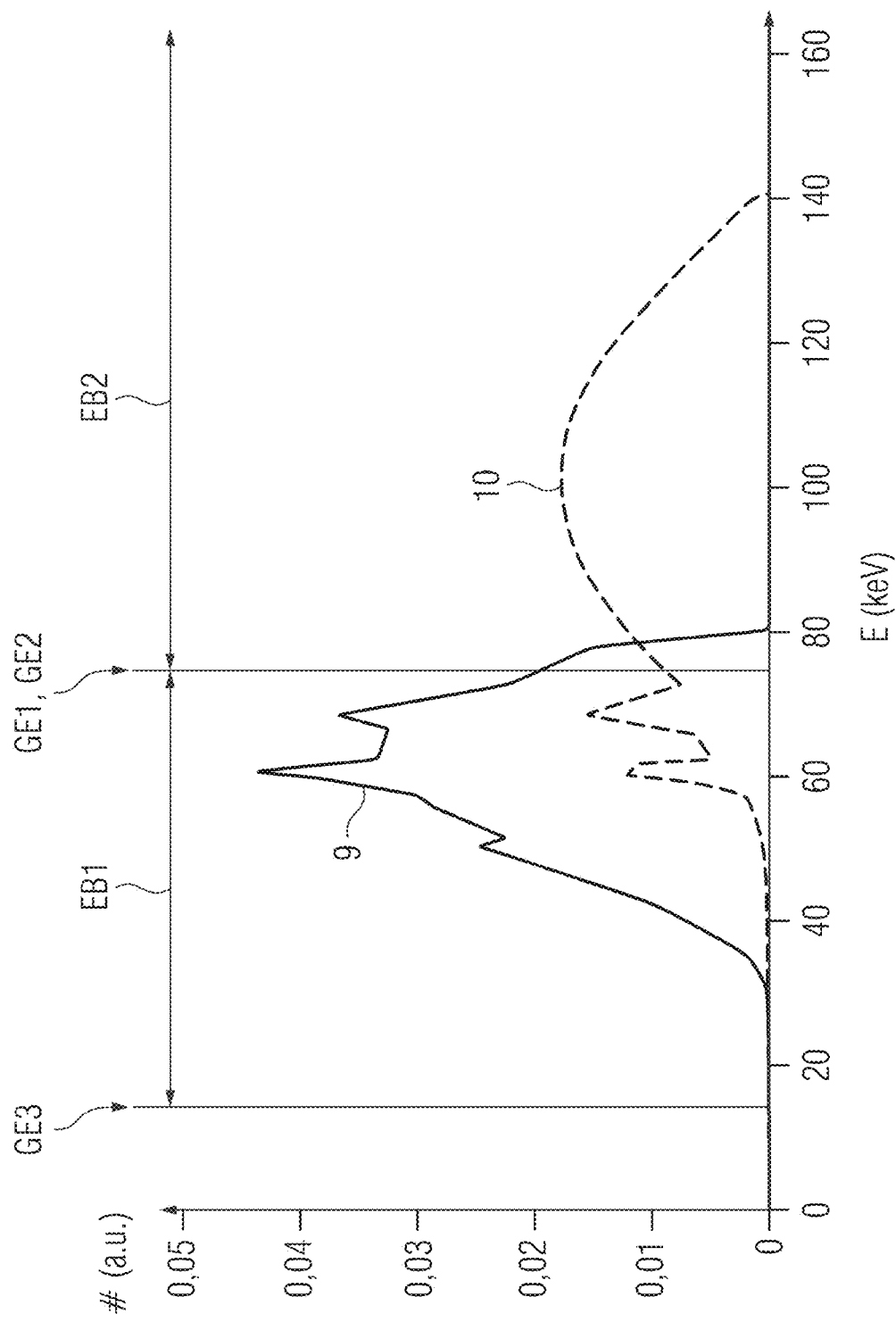
FIG. 2 is a representation of example first and second energy spectra with an example embodiment of first and second energy ranges.
Figure 3:
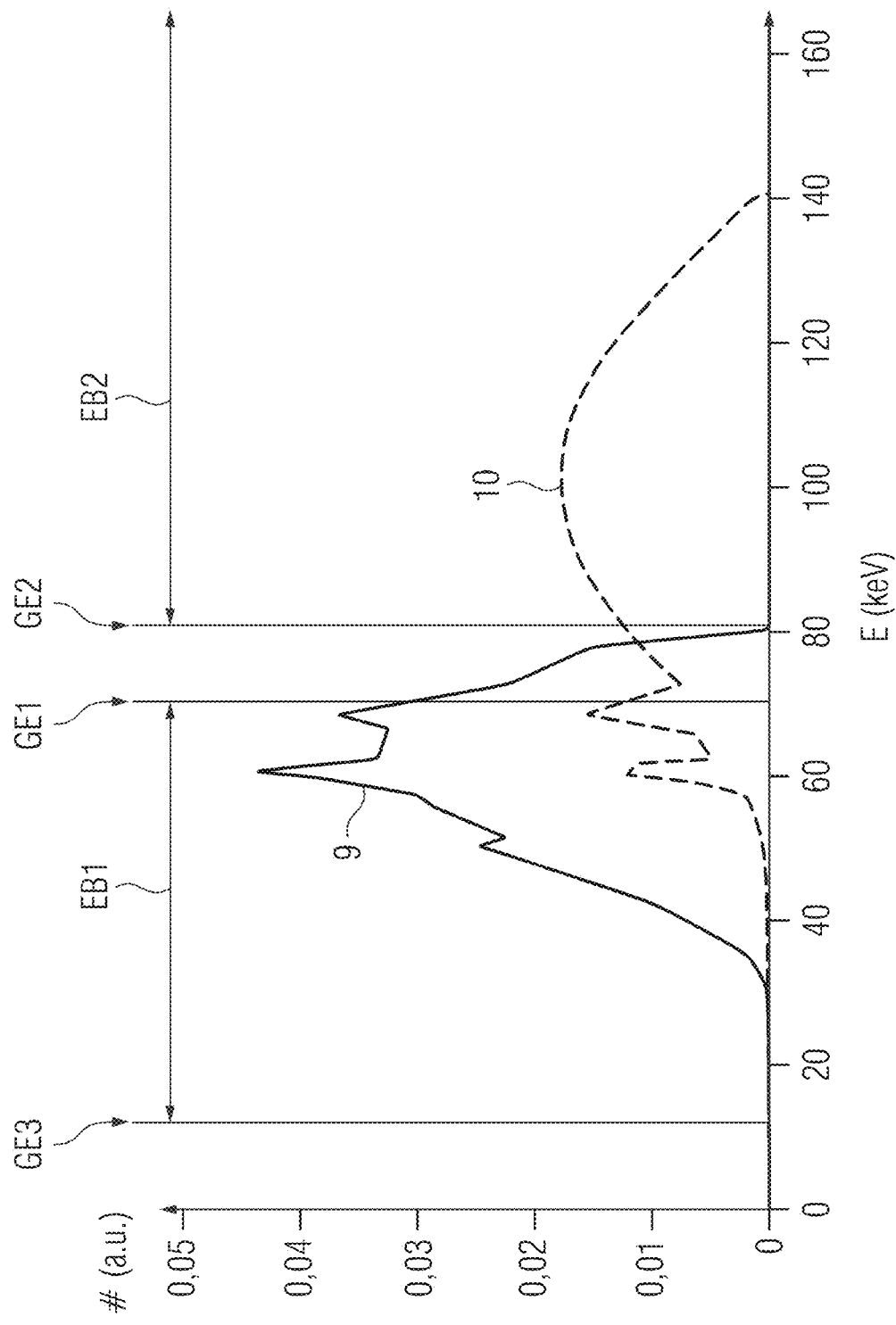
FIG. 3 is a representation of the example first and second energy spectra from FIG. 2 with a further example embodiment of the first and second energy ranges.
Figure 4:
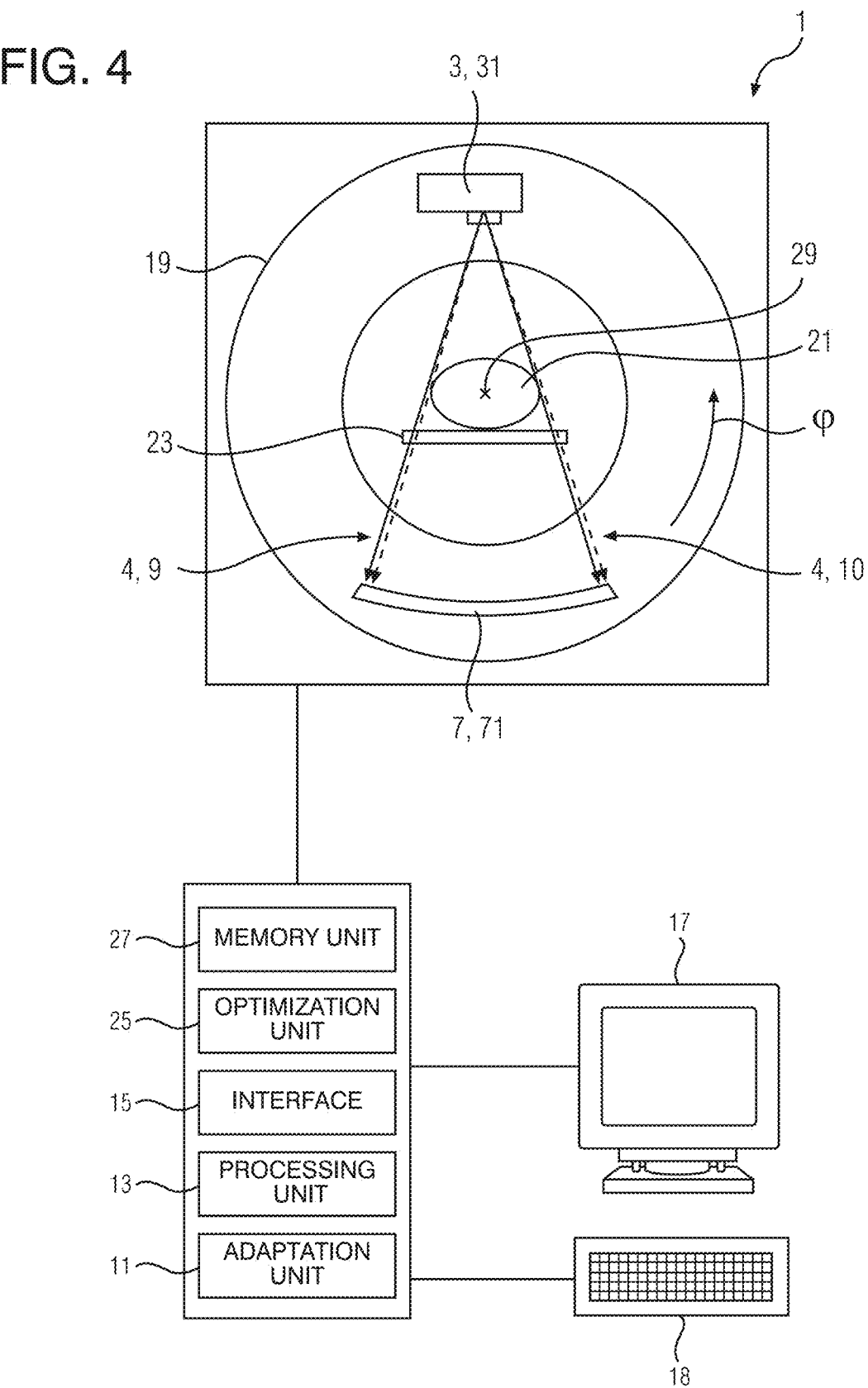
FIG. 4 is a schematic representation of an example embodiment of an apparatus for producing a spectral computed tomography image data set.

FIG. 2 illustrates one possible configuration of the adaptable energy ranges EB1, EB2 after adaptation to the first energy spectrum 9 and the second energy spectrum 10.

An energy spectrum 9, 10 of emitted X-rays substantially describes the distribution of the emitted X-ray photons of an X-ray source as a function of photon energy E. In this example, both energy spectra 9, 10 are in each case based on the use of an X-ray tube with a tungsten anode using two different tube voltages, 80 kV and 140 kV. In this example, a first lower-energy energy spectrum 9 with a maximum photon energy of the emitted X-rays of 80 keV and a second higher-energy energy spectrum 10 with a maximum photon energy of the emitted X-rays of 140 keV are emitted via the X-ray source unit 7. In the case of the second, higher-energy energy spectrum 10, the minimum emitted energy, which substantially contributes to the spectral CT image data set, is moreover shifted to higher energies of between 40 keV and 50 keV via a 0.4 mm tin filter. Different energy spectra may also be used in other variants.

In this setup, the first energy range EB1 is identified as between 15 keV and 75 keV and a second energy range EB2 as above 75 keV. The first, upper limiting energy GE1 of the first energy range EB1 and the second, low-energy limiting energy GE2 of the second energy range EB2 have the same energy value of 75 keV. The first energy range EB1 adjoins the second energy range EB2. The first energy range EB1 is furthermore bounded by a lower limiting energy GE3. It may also be provided that the second energy range EB2 is bounded by an upper limiting energy.

In order to carry out the method according to an embodiment of the invention, at least one first measurement signal is produced as a function of the first energy spectrum 9 and the first energy range EB1 and a second measurement signal as a function of the second energy spectrum 10 and the second energy range EB2.

Such an implementation may for example be implemented with two photon-counting X-ray detectors 73, 74 which in each case have at least two energy thresholds for the generation of energy-resolved measurement signals, in combination with two X-ray sources 33, 34 in the form of a dual-source CT device.

In other words, based upon a dual-source CT device, the two photon-counting X-ray detectors 73, 74 may for example in each case be operated with two energy ranges, wherein the one measuring system consisting of a first X-ray source 33 and the assigned photon-counting X-ray detector 73, which respectively emit and detect the low-energy 80 kV energy spectrum 9, only uses the data of the low-energy energy range EB1 and the other measuring system consisting of the second X-ray source 34 and the assigned photon-counting X-ray detector 74, which respectively emit and detect the higher-energy 140 kV energy spectrum 10, only uses the data of the higher-energy energy range EB2 for production.

Apart from the additional tin filtration of the second energy spectrum 10, a similar implementation is also achievable via a photon-counting X-ray detector 31 which has at least two energy thresholds for the generation of energy-resolved measurement signals, in combination with an X-ray source 31 configured for the kV switching method which emits either the first or the second energy spectrum with a time offset. At least one first measurement signal is here accordingly likewise generated as a function of the first energy spectrum 9 and the first energy range EB1 and a second measurement signal as a function of the second energy spectrum 10 and the second energy range EB2.

It may furthermore moreover be provided that a third measurement signal is generated by the photon-counting X-ray detector(s) as a function of the first energy spectrum 9 and the second energy range EB2 and a fourth measurement signal as a function of the second energy spectrum 10 and the first energy range EB1. The third and fourth measurement signals may then moreover also be included in the production step S5. In this more complex case, the measurement signals of the energy ranges of the photon-counting X-ray detectors may in particular be combined in weighted manner, wherein the third measurement signal is less heavily weighted than the first measurement signal and the fourth measurement signal less heavily weighted than the second measurement signal.

FIG. 2 shows a further example configuration of the energy ranges EB1, EB2 after adaptation to the first energy spectrum 9 and the second energy spectrum 10 from FIG. 2, wherein the first energy range EB1 and the second energy range EB2 are spaced apart from one another.

The lower, low-energy limiting energy GE2 of the second energy range EB2 accordingly has a higher energy value than the upper, higher-energy limiting energy GE1 of the first energy range EB1. In this example, the lower, low-energy limiting energy GE2 of the second energy range EB2 has an energy value of 80 keV corresponding to the maximum emitted energy of the first energy spectrum 9. The upper, higher-energy limiting energy GE1 of the first energy range EB1, in contrast, has an energy value of 70 keV.

Such a configuration may for example be implemented via a photon-counting X-ray detector which has at least three energy thresholds for generating energy-resolved measurement signals and can thus supply a further energy range located in energy terms between the first energy range EB1 and the second energy range EB2.

Such a configuration may for example also be implemented via two photon-counting X-ray detectors, wherein the energy ranges of the first X-ray detector and the second X-ray detector are differently adapted. For example, the first X-ray detector has an energy range, corresponding to the first energy range EB1 according to the invention, located between the limiting energies GE3 and GE1 and an energy range located in energy terms above the limiting energy GE1. For example, the second X-ray detector has an energy range between the limiting energy GE3 and GE2 and an energy range, corresponding to the second energy range EB2 according to the invention, above the limiting energy GE2.

The first measurement signal and the second measurement signal according to an embodiment of the invention are produced for the inventive method at least as a function of the first energy range EB1 according to an embodiment of the invention and the second energy range EB2 according to an embodiment of the invention. Such a configuration with spaced apart energy ranges may optionally enable improved separation of the measurement data based upon the measurement signals.

In addition to the first and the second measurement signals, further measurement signals corresponding to the energy ranges specified by the limiting energies GE1, GE2, GE3 may, however, also be generated as a function of the first energy spectrum 9 and/or second energy spectrum 10. The further energy ranges are preferably included in the production of the spectral CT image data set with a lower weight than the first and the second measurement signals. Other configurations are furthermore also possible. Configurations are, for example, conceivable in which still further energy ranges, which are not shown, are distinguished.

Figure 5:
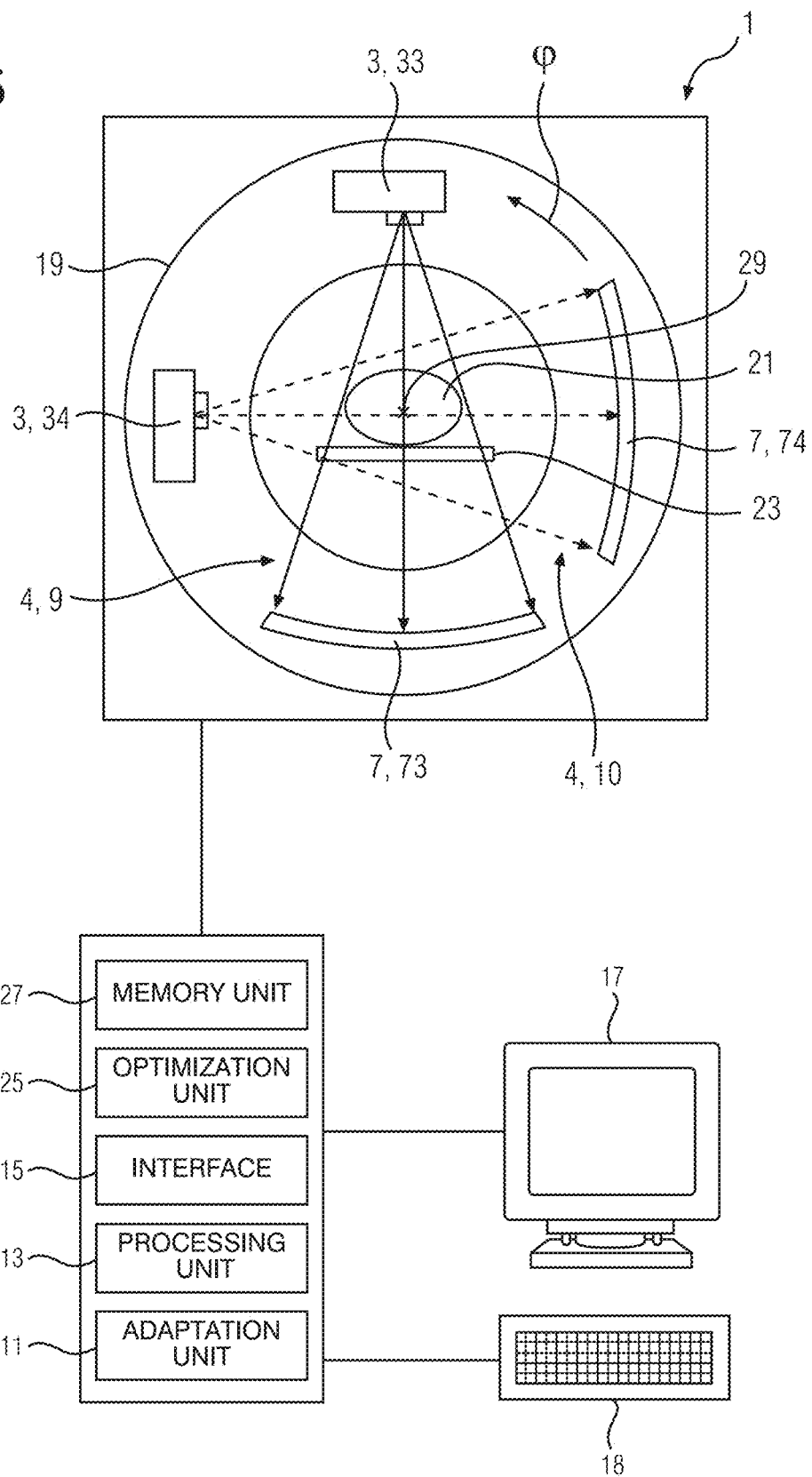
FIG. 5 is a schematic representation of a further example embodiment of an apparatus for producing a spectral computed tomography image data set.

FIG. 5 shows a schematic representation of an apparatus for producing a spectral X-ray image data set, wherein the apparatus is configured as a computed tomography system 1 (CT system).

The CT system 1 comprises a gantry 19 comprising an X-ray source unit 3 with an X-ray source 31 and, opposite, a detection unit 7 with a photon-counting X-ray detector 71. An object under examination 21 is placed on a couch 23 and is movable along the axis of rotation 29 through the gantry opening for recording of the measured projection data. In order to record spatially three-dimensional image data, the X-ray source unit 3 and the detection unit 7 rotates in phi direction about the object 21 to be examined, wherein X-rays 9, 10 are emitted by the X-ray source 31 and, after passing through the object 21, are detected by the X-ray detector 71. During the rotational movement, measurement signals are in each case generated within an angular sector.

The X-ray source unit 3 is in particular configured to emit X-rays 4 having a first energy spectrum 9 and X-rays 4 having a second energy spectrum 10 which differs from the first. In this example, the X-ray source facility 3 has to this end an X-ray source 31, in particular an X-ray tube which is configured to be operated using the "kV switching" method. In other words, while rotating about the object under examination, the X-ray source 31 selectively alternately emits in rapid temporal succession either a first energy spectrum 9 or a second energy spectrum 10, wherein the second energy spectrum 10 differs from the first energy spectrum 9. In general, the X-ray source is operated with two different tube voltages, for example a first lower tube voltage and a second higher tube voltage, such that X-rays with the first, in this case low-energy, energy spectrum and X-rays with the second higher-energy energy spectrum are alternately emitted.

The detection unit 7 has a photon-counting X-ray detector 71 which is positioned opposite the X-ray source 31. During raw data recording, the photon-counting X-ray detector 71 of the detection unit 7 is accordingly alternately illuminated either with the first energy spectrum 9 or with the second energy spectrum 10.

The detection unit 7 is configured to generate measurement signals based upon detected X-rays 4, which measurement signals are resolved at least into a first adaptable energy range EB1 and a second adaptable energy range EB2.

The photon-counting X-ray detector may furthermore also be configured to resolve detected X-rays into further adaptable energy ranges.

The apparatus moreover has an adaptation unit 11 which is configured to adapt the first energy range EB1 and the second energy range EB2 at least as a function of the first energy spectrum 9 and the second energy spectrum 10, wherein in each case at least one limiting energy GE1, GE2 of a respective energy range EB1, EB2 is adapted.

Adaptation as a function of the first energy spectrum and the second energy spectrum may involve selecting and applying the respective at least one limiting energy as a function of the first and the second energy spectra.

It may be provided in one advantageous configuration that the adaptation unit is moreover configured automatically to adapt the respective at least one limiting energy of the first energy range and the second energy range via the adaptation unit as a function of the spectral image processing technique, a type of medical examination and/or an item of patient-specific information.

The apparatus moreover comprises an image processing unit 13 configured to produce the spectral CT image data set via a spectral image processing technique based upon the generated measurement signals, wherein at least the first generated measurement signal is included in the production as a function of the first energy range EB1 and the first energy spectrum 9 and the second generated measurement signal as a function of the second energy range EB2 and the second energy spectrum 10.

If further measurement signals are available, the further measurement signals may correspondingly also be included in production. In particular, the generated measurement signals may here be included in the production of the CT image data set in a manner weighted via weighting factors.

In particular, optimized weighting factors may here be used which are optimized based upon an image noise value of the CT image data set, an image contrast value of the CT image data set or an artifact value of the CT image data set.

The apparatus furthermore comprises an interface 15 configured to output the spectral X-ray image data set. In particular, the spectral CT image data set is output in this example on an output unit 17 in the form of a display unit. The spectral CT image data set can be displayed for an operator via the output unit 17 in the form the display unit.

The apparatus may moreover have an optimization unit 25 which is configured to determine an optimized energy value for the respective at least one limiting energy of the first energy range and the second energy range at least based upon the first and the second energy spectra.

The optimized energy value is preferably here optimized at least with reference to a criterion from the following list:
an image noise value of the CT image data set,
an image contrast value of the CT image data set,
an artifact value of the CT image data set,
a spectral overlap value.

The spectral image processing technique, a type of medical examination and/or an item of patient-specific information may here also be included.

The optimization unit may be configured to determine the optimized energy value based upon a machine learning method, an arithmetic function or calculation or also in another manner.

The adaptation unit 11, the image processing unit 13 and optionally the optimization unit 25 may in particular be implemented in the form of a computer, a microcontroller or an integrated circuit. The adaptation unit 11, the image processing unit 13 and optionally the optimization unit 25 may have hardware elements or software elements, for example a microprocessor or a field programmable gate array (FPGA).

It may also be a computer cluster or cloud.

The apparatus may moreover comprise a memory unit 27. This may take the form of a non-permanent main memory or random access memory (RAM) or as a permanent mass storage device (hard disk, USB stick, SD card, solid state disk). An interface 15 may be a hardware or software interface (e.g. PCI bus, USB or FireWire).

The memory unit may be provided for storing, in a manner retrievable by the adaptation unit, for instance in the form of a database, optimized energy values which have already been determined in advance via the optimization unit for a plurality of first and second energy spectra as a function of the first and second energy spectra, the spectral image processing technique, the type of medical examination and/or patient-specific information or also other parameters.

The memory unit may be provided for retrievably supplying trained or adapted functions which can determine the optimized energy value as a function of the first and second energy spectra, the spectral image processing technique, a type of medical examination and/or an item of patient-specific information or also other parameters as input parameters. These can then be retrieved for the determination step.

Ideally, the apparatus furthermore has at least one input unit 18. An input unit 18 for example enables manual interaction of a user, for example for starting or stopping the method according to an embodiment of the invention. The selection or confirmation of an image processing technique or an X-ray application, or the input of the object under examination or patient-specific information can also be enabled for an operator.

FIG. 5 shows an alternative embodiment of an apparatus according to an embodiment of the invention. In this example, the detection unit 7 has a first photon-counting X-ray detector 73 and, arranged at an angular offset thereto, a second photon-counting X-ray detector 74. The X-ray source unit 3 in each case has opposite thereto a first X-ray source 33 configured to emit the first energy spectrum 9 and has a second X-ray source 34 configured to emit the second energy spectrum 10. This setup corresponds to the previously mentioned dual source CT system.

In this configuration, in particular the first photon-counting X-ray detector 73 is configured to supply at least the first energy range EB1 for energy-resolved measurement signals and to generate at least the first measurement signal as a function of the first energy range EB1 and the first energy spectrum 9. The second photon-counting X-ray detector 74 is then in particular configured to supply at least the second energy range EB2 for energy-resolved measurement signals and to generate at least the second measurement signal as a function of the second energy range EB2 and the second energy spectrum 10. The respective photon-counting X-ray detectors 73, 74 of the detection unit 7 may furthermore also provide still further energy ranges for generating measurement signals which may also be included in the production of the CT image data set.

Figure 6:
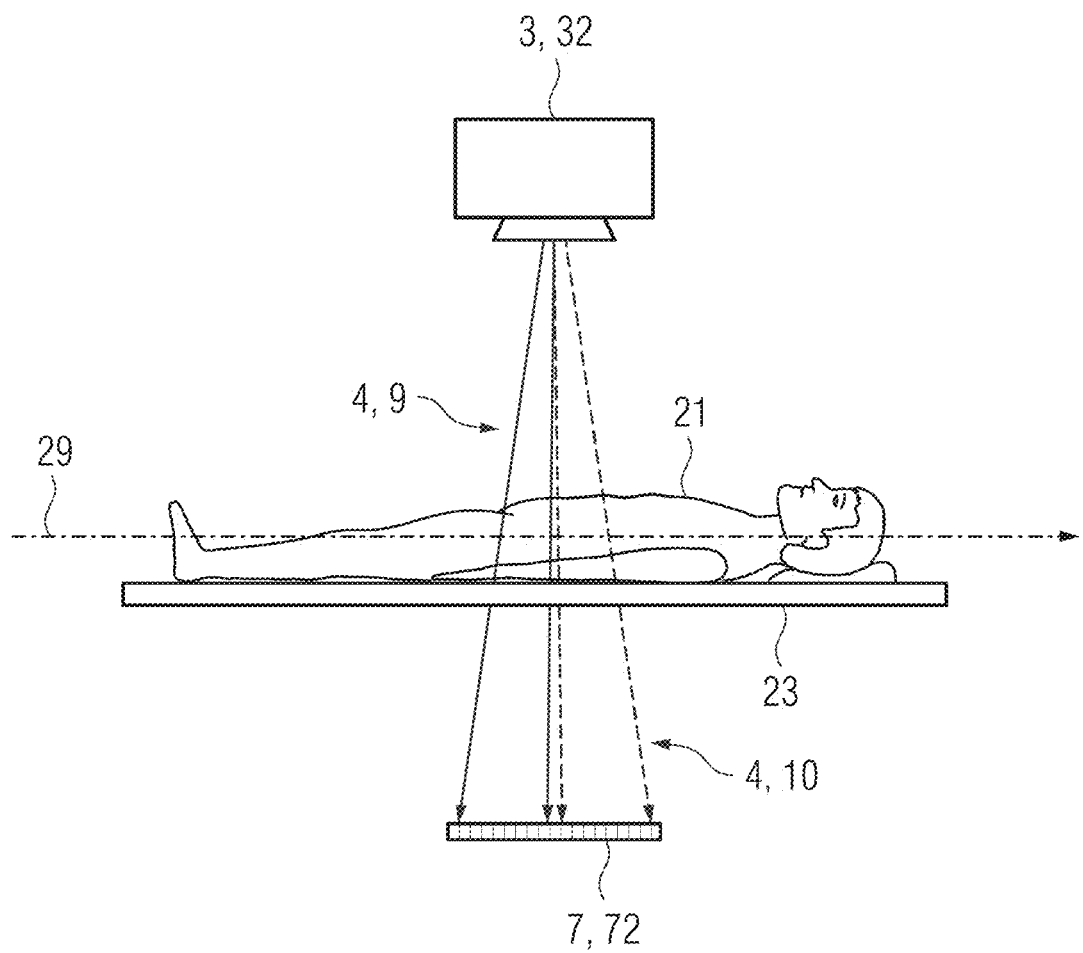
FIG. 6 is a schematic representation of an X-ray source unit and a detection unit for use in a further example embodiment of the apparatus according to the invention for producing a spectral computed tomography image data set.

FIG. 6 is a schematic diagram of a configuration composed of X-ray source unit 3, having an X-ray source 32, and detection unit 7, having a photon-counting X-ray detector 72, as may be used in a further variant of the apparatus according to the invention. In this configuration, the X-ray source 32 is configured with a split filter which constitutes a prefilter divided along the axis of rotation 29, also denoted patient axis, such that two energy spectra which differ from one another, i.e. the first energy spectrum 9 and the second energy spectrum 10, may be simultaneously emitted in different spatial regions via the X-ray source. The photon-counting X-ray detector 72 has a plurality of detection elements, here merely indicated schematically, wherein a first subset of the plurality of detection elements is illuminated via the X-ray source unit 3 with the first energy spectrum 9 and a second subset of the plurality is illuminated with the second energy spectrum 10, such that the first measurement signal may be generated via the first subset of the plurality of detection elements and supplied for production of the spectral CT image data set and the second measurement signal via the second subset of the plurality of detection elements.

The present invention is not limited to the above-described example embodiments. Rather, a person skilled in the art is capable of deriving further embodiments of the invention from the above description. In particular, the individual features of the invention described with reference to the various example embodiments and the variant embodiments thereof may also be combined together in different ways.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a spectral computed tomography image data set via a detection unit including at least one photon-counting X-ray detector and configured to convert detected X-rays into measurement signals, resolved at least into a first adaptable energy range and a second adaptable energy range, and configured to emit, via an X-ray source unit, X-rays having a first energy spectrum and having a second energy spectrum which differs from the first energy spectrum, the method comprising:
    adapting the first adaptable energy range and the second adaptable energy range as a function of the first energy spectrum and the second energy spectrum, respectively, via an adaptation unit, wherein at least one respective limiting energy, of each of a respective one of the first adaptable energy range and the second adaptable energy range, is adapted during the adapting;
    emitting X-rays having the first energy spectrum and emitting X-rays having the second energy spectrum, via the X-ray source unit;
    detecting the X-rays emitted having the first energy spectrum and detecting the X-rays emitted having the second energy spectrum, via the detection unit, wherein at least one first measurement signal is generated as a function of the first adaptable energy range and the first energy spectrum and wherein at least one second measurement signal is generated as a function of the second adaptable energy range and the second energy spectrum;
    producing the spectral computed tomography image data set at least based upon the first measurement signals generated and the second measurement signals generated, with assistance of a spectral image processing technique, via an image processing unit; and
    outputting the spectral computed tomography image data set via an interface.

2. The method of claim 1, wherein the adapting includes:
    automatically adapting, via the adaptation unit, each at least one respective limiting energy of the first adaptable energy range and the second adaptable energy range, as a function of at least one of the spectral image processing technique, a type of medical examination and an item of patient-specific information.

3. The method of claim 2, further comprising:
    determining, via an optimization unit, an optimized energy value for the at least one respective limiting energy of the first adaptable energy range and the second adaptable energy range, at least based upon the first energy spectrum and the second energy spectrum, wherein the optimized energy value includes at least one of:
        an image noise value of the computed tomography image data set,
        an image contrast value of the computed tomography image data set,
        a material contrast value of the computed tomography image data set,
        an artifact value of the computed tomography image data set, and
        a spectral overlap value between at least one of the first energy spectrum and the second adaptable energy range, and the second energy spectrum and the first adaptable energy range.

4. The method of claim 2, wherein the determining comprises application of a machine learning method.

5. The method of claim 2, wherein the first adaptable energy range adjoins the second adaptable energy range.

6. The method of claim 2, wherein the first adaptable energy range and the second adaptable energy range are spaced apart from one another.

7. The method of claim 1, further comprising:
    determining, via an optimization unit, an optimized energy value for the at least one respective limiting energy of the first adaptable energy range and the second adaptable energy range, at least based upon the first energy spectrum and the second energy spectrum, wherein the optimized energy value includes at least one of:
        an image noise value of the computed tomography image data set,
        an image contrast value of the computed tomography image data set,
        a material contrast value of the computed tomography image data set,
        an artifact value of the computed tomography image data set, and
        a spectral overlap value between at least one of the first energy spectrum and the second adaptable energy range, and the second energy spectrum and the first adaptable energy range.

8. The method of claim 1, wherein the determining comprises application of a machine learning method.

9. The method of claim 1, wherein the first adaptable energy range adjoins the second adaptable energy range.

10. The method of claim 1, wherein the first adaptable energy range and the second adaptable energy range are spaced apart from one another.

11. The method of claim 1, wherein a third measurement signal is generated as a function of the first energy spectrum and the second adaptable energy range or as a function of the first energy spectrum and a third adaptable energy range, and wherein a fourth measurement signal is generated as a function of the second energy spectrum and the first adaptable energy range or as a function of the second energy spectrum of a fourth adaptable energy range, and wherein at least one of the third measurement signal and the fourth measurement signal included in the producing.

12. The method of claim 11, wherein during the producing of the spectral computed tomography image data set, the generated measurement signals are included in the image data set in a manner weighted via optimized weighting factors and wherein the first measurement signal is relatively more heavily weighted than the third measurement signal and wherein the second measurement signal relatively more heavily weighted than the fourth measurement signal.

13. The method of claim 12, wherein during the producing of the spectral computed tomography image data set, the generated measurement signals are included in the image data set in a manner weighted via optimized weighting factors and wherein the weighting factors are optimized based upon at least one of:
  an image noise value of the computed tomography image data set,
  an image contrast value of the computed tomography image data set,
  a material contrast value of the computed tomography image data set, and
  an artifact value of the computed tomography image data set.

14. The method of claim 1, wherein during the emitting, either X-rays having the first energy spectrum or X-rays having the second energy spectrum is selectively alternately emitted.

15. The method of claim 1, wherein the detection unit includes a photon-counting X-ray detector with a plurality of detection elements, and wherein a first subset of the plurality of detection elements is illuminated with the first energy spectrum via the X-ray source unit and a second subset of the plurality of detection elements is illuminated with the second energy spectrum, and wherein the first measurement signal is generated via the first subset of the plurality of detection elements and the second measurement signal is generated via the second subset of the plurality of detection elements.

16. The method of claim 1, wherein the detection unit includes a first photon-counting X-ray detector and, arranged at an angular offset, a second photon-counting X-ray detector, and wherein the X-ray source unit includes a first X-ray source arranged opposite the first photon-counting X-ray detector, to emit at the first energy spectrum and includes a second X-ray source arranged opposite the second photon-counting X-ray detector, to emit at the second energy spectrum, and wherein the first measurement signal is generated via the first X-ray detector and the second measurement signal is generated via the second X-ray detector.

17. An apparatus for producing a spectral computed tomography image data set comprising:
  an X-ray source unit configured to emit X-rays having a first energy spectrum and configured to emit X-rays having a second energy spectrum, different from the first energy spectrum;
  a detection unit including at least one photon-counting X-ray detector and configured to generate measurement signals based upon detected X-rays, the measurement signals being resolved at least into a first adaptable energy range and a second adaptable energy range;
  an adaptation unit, configured to adapt the first adaptable energy range and the second adaptable energy range as a function of the first energy spectrum and the second energy spectrum, respectively, wherein at least one limiting energy, of at least one of the first adaptable energy range and the second adaptable energy range, is generated;
  an image processing unit configured to produce the spectral computed tomography image data set using a spectral image processing technique based upon the measurement signals generated, wherein at least one first generated measurement signal is included in production of the spectral computed tomography image data set as a function of the first adaptable energy range and the first energy spectrum and a second generated measurement signal is included in production of the spectral computed tomography image data set as a function of the second adaptable energy range and the second energy spectrum; and
  an interface to output the spectral computed tomography image data set produced.

18. A computed tomography system comprising the apparatus of claim 17.

19. An apparatus for producing a spectral computed tomography image data set comprising:
  an X-ray source configured to emit X-rays having a first energy spectrum and configured to emit X-rays having a second energy spectrum, different from the first energy spectrum;
  a detector including at least one photon-counting X-ray detector and configured to generate measurement signals based upon detected X-rays, the measurement signals being resolved at least into a first adaptable energy range and a second adaptable energy range;
  at least one processor, configured to
    adapt the first adaptable energy range and the second adaptable energy range as a function of the first energy spectrum and the second energy spectrum, respectively, wherein at least one limiting energy, of at least one of the first adaptable energy range and the second adaptable energy range, is generated, and
    produce the spectral computed tomography image data set using a spectral image processing technique based upon the measurement signals generated, wherein at least one first generated measurement signal is included in production of the spectral computed tomography image data set as a function of the first adaptable energy range and the first energy spectrum and a second generated measurement signal is included in production of the spectral computed tomography image data set as a function of the second adaptable energy range and the second energy spectrum; and
  an interface to output the spectral computed tomography image data set produced.

20. A computed tomography system comprising the apparatus of claim 19.

* * * * *